US011154078B2

(12) United States Patent
Seo et al.

(10) Patent No.: US 11,154,078 B2
(45) Date of Patent: Oct. 26, 2021

(54) **LIQUID FOOD COMPOSITION COMPRISING *SOPHORA JAPONICA* EXTRACT**

(71) Applicant: Amorepacific Corporation, Seoul (KR)

(72) Inventors: Dae Bang Seo, Yongin-si (KR); Heeyoung Jeon, Yongin-si (KR); Sun Mi Kim, Yongin-si (KR); Donghyun Cho, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 259 days.

(21) Appl. No.: 16/547,898

(22) Filed: Aug. 22, 2019

(65) Prior Publication Data

US 2020/0100527 A1 Apr. 2, 2020

(30) Foreign Application Priority Data

Sep. 28, 2018 (KR) .................. 10-2018-0116270

(51) Int. Cl.
*A23L 2/02* (2006.01)
*A23L 29/269* (2016.01)
*A23L 33/105* (2016.01)
*A23L 2/52* (2006.01)

(52) U.S. Cl.
CPC .................. *A23L 2/02* (2013.01); *A23L 2/52* (2013.01); *A23L 29/27* (2016.08); *A23L 33/105* (2016.08)

(58) Field of Classification Search
CPC ........... A23L 2/02; A23L 29/27; A23L 33/105

USPC ......................... 426/599, 634, 648, 615, 573
See application file for complete search history.

(56) References Cited

U.S. PATENT DOCUMENTS

| 5,240,732 A | 8/1993 | Ueda |
| 2008/0199545 A1 | 8/2008 | Krempin et al. |
| 2008/0286421 A1 | 11/2008 | DeLease et al. |

FOREIGN PATENT DOCUMENTS

| CN | 1709116 A | 12/2005 |
| KR | 10-0772575 B1 | 11/2007 |
| KR | 10-0879032 B1 | 1/2009 |
| KR | 10-2011-0004603 A | 1/2011 |
| KR | 10-2014-0036966 A | 3/2014 |
| KR | 10-2014-0114801 A | 9/2014 |
| KR | 10-2017-0050160 A | 5/2017 |
| KR | 10-1875466 B1 | 7/2018 |
| WO | 2008/010663 A1 | 1/2008 |
| WO | 2008/051594 A2 | 5/2008 |
| WO | 2009/089326 A2 | 7/2009 |
| WO | WO 2010/11174545 | * 10/2010 |

\* cited by examiner

*Primary Examiner* — Helen F Heggestad
(74) *Attorney, Agent, or Firm* — Sughrue Mion, PLLC

(57) ABSTRACT

The present invention relates to a liquid food composition comprising a *Sophora japonica* and a broad-leaf bamboo extract, and more particularly, to a liquid food composition including a *Sophora japonica* extract, a broad-leaf bamboo extract, and xanthan gum. The liquid food composition includes a high content of the *Sophora japonica* extract while simultaneously ensuring the liquid properties, and thus can be used widely in the field of foods because the liquid food composition is applicable to liquid formulations.

7 Claims, 2 Drawing Sheets

LIQUID FOOD COMPOSITION COMPRISING *SOPHORA JAPONICA* EXTRACT

CROSS-REFERENCE TO RELATED APPLICATION

This application claims the benefit of Korean Patent Application No. 10-2018-0116270 on Sep. 28, 2018 with the Korean Intellectual Property Office, the disclosure of which is incorporated herein by reference in its entirety.

BACKGROUND

1. Field of the Invention

The present invention relates to a liquid food composition including a *Sophora japonica* extract.

2. Discussion of Related Art

*Sophora japonica* is a deciduous tree that belongs to the family Leguminosae, grows in Korea, Japan, and China, and has been used as medicine because it has various pharmacological effects of alleviating fevers, exerting astriction, stopping bleeding, soothing the pain, preventing hypertension, hyperlipidemia, and the like.

A *Sophora japonica* fruit, also known as Sophorae fructuse, contains a significant amount of isoflavones. Isoflavones are components that are similar to female hormones (i.e., estrogen, etc.), and are known to be effective in relieving the menopausal symptoms when the hormone replacement therapy is used to relax the female menopause. Also, the isoflavones are known to be effective in preventing osteoporosis and bone fracture and preventing and treating breast cancer and prostate cancer. In addition, because it is identified that the *Sophora japonica* fruit contains a highly significant amount of polyphenols, such a fruit is known to be effective in preventing aging through the antioxidant and active oxygen-releasing activities of the polyphenols.

As described above, although *Sophora japonica* includes a number of substances that serve to prevent the aging, exert anticancer and antioxidant activities, and improve the health (in the case of components for female hormone replacement therapy), and the like, most of the substances are water-insoluble substances that not completely soluble in water, or are not easily dispersed even when the corresponding substances are soluble in water. Therefore, such substances have been formulated into solid phases in the form of tablets, capsules, and the like due to the problems in their processing qualities. Meanwhile, only small amounts of the substances are added when formulated in a liquid phase because they have an ability to form a precipitate from the active ingredient of *Sophora japonica*.

Accordingly, lots of research and development of *Sophora japonica* have been conducted in order to apply the *Sophora japonica* to various formulations of foods, drugs, cosmetics, and the like.

For example, Korean Patent Application Publication No. 2011-0004603 discloses that the use of the *Sophora japonica* extract obtained through extraction with 75 to 85% (v/v) of ethanol at room temperature for 10 to 24 hours enhances the utilities for foods or cosmetics.

Also, Korean Patent Registration No. 10-1875466 discloses the technology for preparing pills using a *Sophora japonica* powder.

Although these patents propose the probability of using *Sophora japonica* in various products, they have drawbacks in that *Sophora japonica* generally has very low contents of the active ingredients. In recent years, there is an increasing the consumers' demand for various health functional food formulations as well. In particular, the interest in liquid drink formulations is rising due to the ease of drinking and the high preference. Therefore, there is need for development of liquid food compositions including a high content of the *Sophora japonica* extract while simultaneously exhibiting excellent properties such as dispersibility, homogeneity, and fluidity.

PRIOR-ART DOCUMENTS

Patent Documents

Korean Patent Application Publication No. 2011-0004603 (Jan. 14, 2011) entitled "Extracts from *Sophora Japonica* L. for Treating or Preventing Menopausal Complaints, Skin Aging, or Skin Wrinkles"

Korean Patent Registration No. 10-1875466 (Jul. 2, 2018) entitled "Method of Preparing Pills for Health Functional Foods Using *Sophora japonica* L."

SUMMARY OF THE INVENTION

Technical Problem

Therefore, the present inventors have conducted lots of research to solve the above problems, and found that, when a liquid food composition includes a broad-leaf bamboo extract and xanthan gum as well as the *Sophora japonica* extract, the liquid food composition includes a high content of the *Sophora japonica* extract, while simultaneously stably maintaining the liquid properties, by regulating a content of the xanthan gum. Therefore, the present invention has been completed based on these facts.

Accordingly, an object of the present invention is to provide a liquid food composition including a *Sophora japonica* extract, which has excellent dispersibility, fluidity, and homogeneity.

Another object of the present invention is to provide a food including the liquid food composition.

Technical Solution

According to an aspect of the present invention, there is provided a liquid food composition comprising a *Sophora japonica* extract, a broad-leaf bamboo extract, and xanthan gum.

The *Sophora japonica* extract may be a *Sophora japonica* fruit extract.

The *Sophora japonica* extract may be included in an amount of from 0.1 to 4% by weight, based on a total of 100% by weight of the liquid food composition.

The broad-leaf bamboo extract may be included in an amount of from 0.1 to 5% by weight, based on a total of 100% by weight of the liquid food composition.

The xanthan gum may be included in an amount of from 0.01 to 0.15% by weight, based on a total of 100% by weight of the liquid food composition.

The liquid food composition may have a viscosity at 25° C. ranging from 1 to 50 cPs.

According to another aspect of the present invention, there is provided a food including the liquid food composition.

Advantageous Effects

A liquid food composition according to the present invention can be stably dispersed while including a high amount of the *Sophora japonica* extract and does not cause precipitation or gelation, so that the fluidity can be maintained in accordance with the flow of the liquefied products. Therefore, the liquid food composition of the present invention is easy to apply to liquid formulations.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
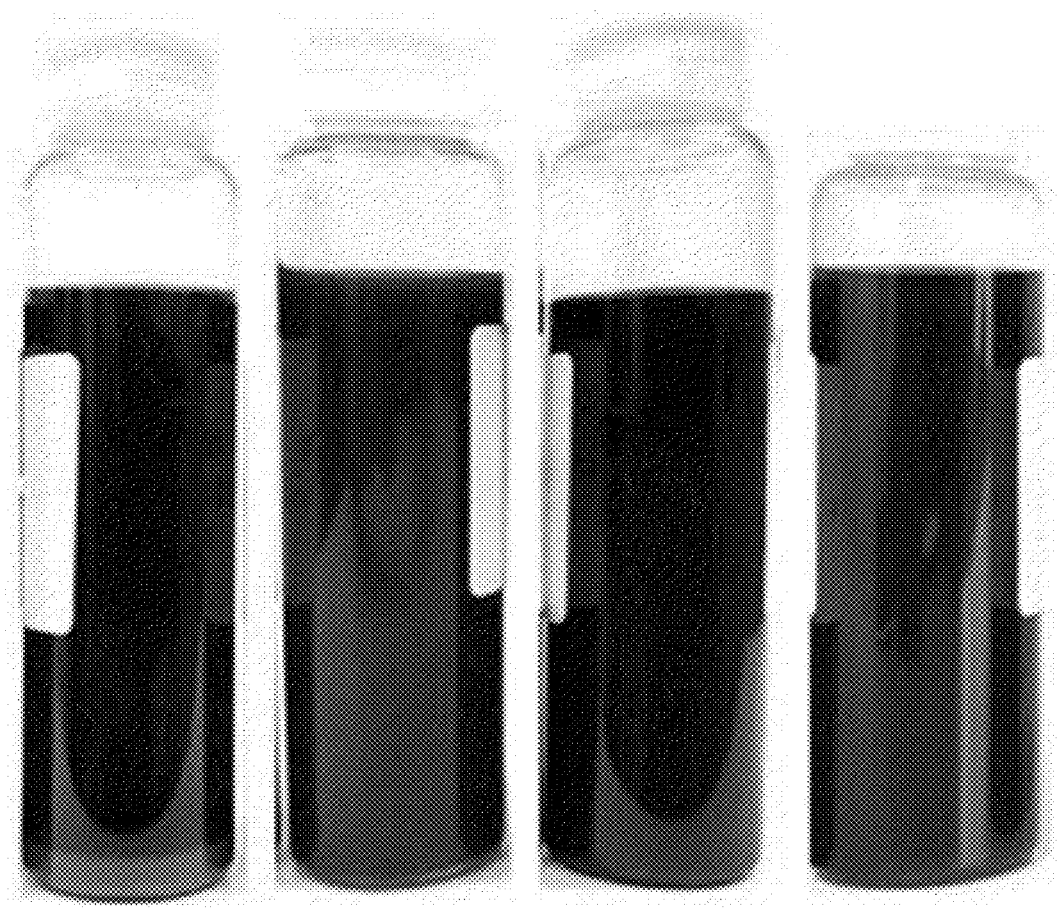
FIG. 1 is an image for evaluating the dispersibility and homogeneity of a liquid food composition according to Experimental Example 1 of the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

*Sophora japonica* has been used long before because it has antibacterial, antioxidant, anti-aging, and anti-cancer activities, and has an effect of preventing various adult diseases, and the like. In particular, various studies show that a large amount of isoflavones included in the *Sophora japonica* extract are effective in relieving female menopausal symptoms and treating and preventing female menopausal disorders.

However, because the *Sophora japonica* extract including water-insoluble compounds such as isoflavones is insoluble in water, it is difficult to prepare liquid products, such as drinks, which includes the *Sophora japonica* extract. Also, because the *Sophora japonica* extract is easily precipitated even when the extract includes small amounts of the water-insoluble compounds, the *Sophora japonica* extract is just applicable to the restrictive shapes of formulations.

For this purpose, a liquid composition is prepared by mixing the *Sophora japonica* extract with a thickening agent such as xanthan gum, as known in the prior art. However, the *Sophora japonica* extract has a poor effect of improving the dispersibility or stability when the xanthan gum is used at a low concentration, whereas the *Sophora japonica* extract may be gelled to form a rigid solid phase when the xanthan gum is used at a high concentration, which results in degraded liquid properties.

In view of the above, the present invention provides a liquid food composition, which is effectively applicable to products such as liquid formulations, by dispersing the *Sophora japonica* extract through the xanthan gum and the broad-leaf bamboo extract in a liquid so that the liquid food composition includes a high content of the *Sophora japonica* extract while simultaneously maintaining the fluidity of the liquid composition.

The liquid food composition according to one exemplary embodiment of the present invention comprises a *Sophora japonica* extract, a broad-leaf bamboo extract, and xanthan gum.

In the present invention, the *Sophora japonica* extract refers to an extract obtained from all parts of *Sophora japonica*, such as leaves, flowers, fruits, seeds, stems, roots, barks, and the like, and the extracted parts of *Sophora japonica* are not limited the specific parts thereof.

The *Sophora japonica* is a tree that belongs to the family Leguminosae, has a characteristic of spreading branches with green branchlets and smelling when cut therein, and also has alternate leaves with one pinnate leaf. Also, it has 1 to 17 leaflets, is in an oval or ellipse shape, and has small petioles and lying hairs on the underside of leaves, and its pale yellow flowers blossom in August, and are in a paniculate shape. Pods grow to 5 to 8 cm in length, and contain seeds formed with slender grooves in a drooping shape.

The *Sophora japonica*' buds are referred to as *sophora* flowers, and its fruits are referred to as Sophorae fructus, both of which are used for medicinal purposes. The fruits are legumes that have a cylindrical or bead shape, and the fleshes are used to treat hemorrhoids when used in combination with its branches and barks. Also, its garden trees or woods are often used as furniture materials. Meanwhile, the known use of the *sophora* flowers includes the treatment or prevention of arteriosclerosis and hypertension, and the *sophora* flowers are also used to have beer and paper dyed yellow.

Among such contents of *Sophora japonica*, the *Sophora japonica*' fruits have effects of suppressing cancer cells, relieving the symptoms of menopausal disorders, preventing aging, etc., has innate colors and flavors, and has no tastes and odors, and thus are suitable for use in food compositions.

As described above, the *Sophora japonica* extract of the present invention is derived from *Sophora japonica*, and thus may be extracted and used without any limitation of its contents. However, it is preferable to make use of a *Sophora japonica* fruit, that is, a Sophorae fructus extract in terms of the pharmacological effects or qualities.

The *Sophora japonica* extract may be prepared according to conventional methods known in the related art, which include extracting an active ingredient from a natural substance. In general, the extract refers to a material obtained by extraction of active ingredients from the natural substance, and encompasses all kinds of ingredients regardless of the extraction methods or the types of components. Therefore, for example, the extract is construed as having a broad concept of encompassing those obtained by extracting components, which are dissolved in a solvent, from natural substances using water or an organic solvent, those obtained by extracting only a certain component of a natural substance, etc.

In this case, the *Sophora japonica* used for extraction may be collected, followed by washing for use intact, or drying for use. In this case, the drying method that may be used herein includes all types of sun drying, shade drying, hot-air drying, and natural drying methods. Also, *Sophora japonica* or a dried product thereof may be ground using a grinding machine, and used to enhance the extraction efficiency.

For example, the *Sophora japonica* extract of the present invention may be extracted by means of a solvent extraction method.

In this case, the solvent that may be used herein includes at least one selected from the group consisting of water; $C_1$~$C_5$ lower alcohols such as methanol, ethanol, isopropyl alcohol, n-propyl alcohol, n-butanol, and isobutanol; polyhydric alcohols such as glycerol, ethylene glycol, propylene glycol, 1,3-butylene glycol, etc.; hydrocarbon-based solvents such as acetone, methyl acetate, ethyl acetate, benzene, n-hexane, diethyl ether, dichloromethane, chloroform, etc.; and non-polar organic solvents such as petroleum ether, methyl acetate, benzene, hexane, chloroform, methylene chloride, dimethyl ether, ethyl acetate, etc. Preferably, the *Sophora japonica* extract may be extracted using at least one selected from the group consisting of water, a $C_1$~$C_5$ lower alcohol, and acetone.

When the extract is prepared by means of the solvent extraction method, the conventional methods such as hot-water extraction, cold extraction, high-pressure extraction, ultrasonic extraction, reflux extraction, supercritical extraction, and the like may be used. In this case, the extraction temperature and the extraction time may vary depending on an object to be used for extraction, and a method, and the like, and may be chosen within appropriate ranges by those skilled in the related art. In addition, the extraction may be performed once or several times in an hour to several days. Also, when the shaking is performed during the extraction by means of a shaker, the extraction efficiency may be further enhanced.

As a process of removing floating solid particles from the extract, a method of filtering particles using cotton, nylon, and the like, an ultrafiltration method, a cold filtration method, a centrifugation method, or the like may be used, but the present invention is not limited thereto. Also, such a method may further include a separation or purification process using various types of chromatography (size, electric charge, hydrophobicity, or affinity chromatography).

For example, the *Sophora japonica* extract may refer to a product obtained by dipping the *Sophora japonica* fruit and a dried or processed product thereof in various solvents, followed by extracting the resulting mixture for a predetermined period of time. In this case, the resulting product may be used intact in a liquid phase, or may be concentrated and/or dried, and then used. The concentration and/or drying method includes method such as freeze-drying, vacuum drying, hot-air drying, spray drying, drying under reduced pressure, foam drying, high-frequency drying, infrared drying, and the like, but the present invention is not limited thereto. Therefore, the *Sophora japonica* extract includes all types of the extract obtained using the solvent, as well as purified products thereof, or concentrated, diluted or dried forms of the extract or purified products thereof.

The *Sophora japonica* extract may be included in an amount of from 0.1 to 4% by weight, preferably from 0.5 to 3% by weight, based on a total of 100% by weight of the liquid food composition. When the *Sophora japonica* extract is included within the amount range as described above, it is possible to sufficiently ensure a pharmacological effect of the *Sophora japonica* extract. Also, most of the conventional compositions including the *Sophora japonica* extract are in a solid phase, as described above. When the compositions are in a liquid phase, it is difficult for the compositions to include a high content of the *Sophora japonica* extract. In comparison, the composition according to the present invention may include a high content of the *Sophora japonica* extract while simultaneously maintaining stable liquid properties. According to embodiments, the *Sophora japonica* extract content in the liquid food composition may be about 0.1%, 0.2%, 0.3%, 0.4%, 0.5%, 0.6%, 0.7%, 0.8%, 0.9%, 1%, 2%, 3%, or 4% by weight, based on a total of 100% by weight of the liquid food composition.

In the present invention, the broad-leaf bamboo extract includes phytochemicals such as curmaric acid, chlorogenic acid, and the like, and some protein and fatty components. In particular, because carbohydrates included therein contain pectin components structurally derived from stems and leaves of a plant, these components serve to help crosslinking and thickening actions to inhibit precipitation of insoluble substances, thereby ensuring the homogeneity of and further increasing the commercial value of the composition of the present invention.

As described above, the broad-leaf bamboo extract refers to an extract obtained from all parts of the broad-leaf bamboo, such as leaves, flowers, fruits, seeds, stems, roots, barks, and the like, and the extracted parts of the broad-leaf bamboo are not limited the specific parts thereof.

The broad-leaf bamboo is an indigenous tree that has a scientific name of *Sasa quelpaertensis Nakai* and grows in a restricted region around Mt. Hallasan in Jeju Island. Also, the broad-leaf bamboo grows to form large colonies in the distribution areas, and its shapes are characteristically distinct from those of Northern bamboo (scientific name: *Sasa borealis* (Hack.) Makino & Shibata) living in the inland areas in Korea. When the Jeju Island suffered from the famine of foods, the broad-leaf bamboo has been used for long as a hardy plant resource because the broad-leaf bamboo fruits contain a large amount of storage starch in terms of the resource plants science. Therefore, the broad-leaf bamboo is a plant that has a high probability of being used as a resource plant.

The broad-leaf bamboo extract may be prepared according to conventional methods known in the related art, which include extracting an active ingredient from a natural substance. In general, the extract refers to a material obtained by extraction of active ingredients from the natural substance, and encompasses all kinds of ingredients regardless of the extraction methods or the types of components. Therefore, for example, the extract is construed as having a broad concept of encompassing those obtained by extracting components, which are dissolved in a solvent, from natural substances using water or an organic solvent, those obtained by extracting only a certain component of a natural substance, etc.

In this case, the broad-leaf bamboo used for extraction may be collected, followed by washing for use intact, or drying for use. In this case, the drying method that may be used herein includes all types of sun drying, shade drying, hot-air drying, and natural drying methods. Also, the broad-leaf bamboo or a dried product thereof may be ground using a grinding machine, and used to enhance the extraction efficiency.

For example, the broad-leaf bamboo extract of the present invention may be extracted by means of a solvent extraction method.

In this case, the solvent that may be used herein includes at least one selected from the group consisting of water; $C_1$~$C_5$ lower alcohols such as methanol, ethanol, isopropyl alcohol, n-propyl alcohol, n-butanol, and isobutanol; polyhydric alcohols such as glycerol, ethylene glycol, propylene glycol, 1,3-butylene glycol, etc.; hydrocarbon-based solvents such as acetone, methyl acetate, ethyl acetate, benzene, n-hexane, diethyl ether, dichloromethane, chloroform, etc.; and non-polar organic solvents such as petroleum ether, methyl acetate, benzene, hexane, chloroform, methylene chloride, dimethyl ether, ethyl acetate, etc. Preferably, the broad-leaf bamboo extract may be extracted using at least one selected from the group consisting of water, a $C_1$~$C_5$ lower alcohol, and acetone.

When the extract is prepared by means of the solvent extraction method, the conventional methods such as hot-water extraction, cold extraction, high-pressure extraction, ultrasonic extraction, reflux extraction, supercritical extraction, and the like may be used. In this case, the extraction temperature and the extraction time may vary depending on an object to be used for extraction, and a method, and the like, and may be chosen within appropriate ranges by those skilled in the related art. In addition, the extraction may be performed once or several times in an hour to several days. Also, when the shaking is performed during the extraction by means of a shaker, the extraction efficiency may be further enhanced.

As a process of removing floating solid particles from the extract, a method of filtering particles using cotton, nylon, and the like, an ultrafiltration method, a cold filtration method, a centrifugation method, or the like may be used, but the present invention is not limited thereto. Also, such a method may further include a separation or purification process using various types of chromatography (size, electric charge, hydrophobicity, or affinity chromatography).

For example, the broad-leaf bamboo extract may refer to a product obtained by dipping a dried or processed product of broad-leaf bamboo in various solvents, followed by extracting the resulting mixture for a predetermined period of time. In this case, the resulting product may be used intact in a liquid phase, or may be concentrated and/or dried, and then used. The concentration and/or drying method includes method such as freeze-drying, vacuum drying, hot-air drying, spray drying, drying under reduced pressure, foam drying, high-frequency drying, infrared drying, and the like, but the present invention is not limited thereto. Therefore, the broad-leaf bamboo extract includes all types of the extract obtained using the solvent, as well as purified products thereof, or concentrated, diluted or dried forms of the extract or purified products thereof.

The broad-leaf bamboo extract may be included in an amount of from 0.1 to 5% by weight, preferably from 1 to 3% by weight, based on a total of 100% by weight of the liquid food composition. When the amount of the broad-leaf bamboo extract is less than the above range, it is difficult to avoid a precipitation phenomenon. On the other hand, when the amount of the broad-leaf bamboo extract is over the above range, the broad-leaf bamboo extract may be gelled due to the increased viscosity, resulting in degraded liquid qualities. According to embodiments, the broad-leaf bamboo extract content in the liquid food composition may be about 0.1%, 0.2%, 0.3%, 0.4%, 0.5%, 0.6%, 0.7%, 0.8%, 0.9%, 1%, 2%, 3%, 4%, or 5% by weight, based on a total of 100% by weight of the liquid food composition.

In the present invention, the xanthan gum is a thickening agent that serves to stably disperse the aforementioned *Sophora japonica* extract in the solvent. In general, the thickening agent in the liquid composition is widely used to form a texture of food or improve the properties, that is, to require the viscosity, form a gel, or improve the dispersion stability. However, as described above, the xanthan gum has a drawback in that it is difficult to determine an appropriate concentration range for use, as known in the prior art. Meanwhile, the composition according to the present invention may include a high content of the *Sophora japonica* extract while simultaneously stably dissolving the *Sophora japonica* extract in a solvent using a certain concentration of a thickening agent (i.e., xanthan gum), and thus may ensure the dispersibility and also prevent gel formation, thereby maintaining the liquid properties such as fluidity.

The xanthan gum may be included in an amount of from 0.01 to 0.15% by weight, preferably from 0.02 to 0.1% by weight, based on a total of 100% by weight of the liquid food composition. When the amount of the xanthan gum is less than the above range, the *Sophora japonica* extract may not be stably dissolved, resulting in degraded dispersibility. On the other hand, when the amount of the xanthan gum is over the above range, the composition may be gelled due to an excessively increased viscosity thereof. According to embodiments, the xanthan gum content in the liquid food composition may be about 0.01%, 0.02%, 0.03%, 0.04%, 0.05%, 0.06%, 0.07%, 0.08%, 0.09%, 0.1%, 011%, 0.12%, 0.13%, 0.14%, or 0.15% by weight, based on a total of 100% by weight of the liquid food composition.

The liquid food composition according to one exemplary embodiment of the present invention includes a higher content of the *Sophora japonica* extract as the active ingredient, compared to the conventional food compositions, while simultaneously stably dissolving the *Sophora japonica* extract, and thus may have excellent dispersibility, and also may consistently maintain the liquid properties of the liquid food compositions. In this case, the liquid properties of the liquid food compositions refer to the extent of properties which do not hinder the convenience that a consumer feels when the consumer eats the liquid food composition because the liquid food composition has fluidity corresponding to the flow of a liquid-phase composition. Also, the liquid food composition according to one exemplary embodiment of the present invention may include the broad-leaf bamboo extract, and thus may avoid a precipitation phenomenon, thereby maintaining the composition in a homogeneous state. In this case, the term "homogeneous state" refers to a state in which there is no problem in qualities because the components are not separated and there are no solid contents (for example, aggregates). In addition, the liquid food composition of the present invention has advantages in that it has small changes in properties due to the solidification and precipitation even when stored for a long period of time, which makes it possible to maintain the liquid properties for a long period of time, thereby resulting in excellent stability of products.

Specifically, the liquid food composition according to the present invention has a viscosity at 25° C. ranging from 1 to 50 cPs, so that the liquid food composition maintains the fluidity exhibited by liquefied products. Also, the liquid food composition of the present invention exhibits excellent homogeneity, and maintains similar levels of dispersibility, fluidity and homogeneity even when the liquid food composition is stored for a period of time.

Also, the present invention provides a food including the liquid food composition.

The food refers to a natural substance or processed product that contains one or more nutrients, preferably to a state in which one can directly eat as a food after a certain processing process. Also, the food includes various foods, drinks (e.g., fruits, vegetable drink, soybean milk products, fermented drinks, etc.), special nutrient foods (e.g., milk formulas, baby foods, liquid foods, etc.), processed meat products, fish products, Tofu, jellied foods, noodles (e.g., Ramen, noodles etc.), health food supplements, seasoning foods (e.g., soy sauce, fermented soybean paste sauce, red pepper paste sauce, mixed paste sauce, etc.), sauces, confectionery (e.g., snacks), milk products (e.g., fermented milk, cheese etc.), other processed foods, Kimchi, salted foods (various kinds of Kimchi, pickled vegetables etc.), natural seasonings (e.g., Ramen soup etc.), and the like, but the present invention is not limited thereto. The food may be prepared using conventional preparation methods.

When the liquid food composition according to the present is used for foods, the liquid food composition may include other components that may have a synergistic effect on the main effects within a range having no harm to the desired main effects of the present invention. For example, the liquid food composition may further include additives such as fragrances, natural pigments, disinfectants, antioxidants, preservatives, moisturizing agents, thickening agents, inorganic salts, emulsifying agents, and synthetic polymer materials so as to improve the properties. In addition, the liquid food composition may further include auxiliary components such as water-soluble vitamins, oil-soluble vitamins, polymeric peptides, polymeric polysaccharides, and seaweed extracts. Those skilled in the related art may choose and mix the components without any difficulty according to the formulations and purposes of use thereof. In this case, amounts of the components added may be selected within a range having no harm to the objects and effects of the present invention.

The food formulations may be in various forms of solutions, emulsions, viscous mixtures, tablets, powders, and the like. Preferably, the food formulations may be in a liquid state such as a solution and an emulsion. For example, the food may be a drink, a concentrate, a dietary convenience food, a spray, or a liquid food.

The drink refers to all types of beverages that one drinks to quench the thirst or enjoy the taste, and is intended to include functional drinks. The drink may include, as an essential component, the liquid food composition of the present invention including a given proportion of the *Sophora japonica* extract as the active ingredient, and also may include other components without any limitation. In this case, the drink may contain various flavoring agents or natural carbohydrates as the same additional components as used in the conventional drinks. Examples of the aforementioned natural carbohydrates include conventional sugars, such as monosaccharides, for example glucose, fructose, and the like; disaccharides, for example maltose, sucrose, and the like; and polysaccharides, for example dextrin, cyclodextrin, and the like, and sugar alcohols such as xylitol, sorbitol, erythritol, and the like. In addition to the components as described above, natural flavoring agents (thaumatin, stevia extracts (for example, rebaudioside A, glycyrrhizin, etc.), and synthetic flavoring agents (saccharin, aspartame, etc.) may be favorably used as the flavoring agents. In general, a proportion of the natural carbohydrate may be in a range of approximately 1 to 20 g, preferably 5 to 12 g per 100 mL of the composition of the present invention. In addition, the composition of the present invention may further include fleshes for preparing a natural fruit juice, a fruit juice drink, a vegetable drink, and the like.

In the food according to the present invention, the content of the liquid food composition, particularly an amount of the *Sophora japonica* extract as the active ingredient, may vary depending on the contents of the food, the type of formulations, and the like. For example, a drink may be included at an amount of 10 to 400 mL, preferably 20 to 100 mL.

Hereinafter, the present invention will be described in detail with reference to Examples thereof. However, it should be understood that these Examples are provided to help better understanding of the present invention, and the present invention is not limited thereto without departing from the scope of the present invention, as apparent to those skilled in the art.

EXAMPLES AND COMPARATIVE EXAMPLES

Example 1

100 kg of a *Sophora japonica* fruit was ground to 60 meshes using a dry grinding machine. The ground product was extracted by adding an amount of ethanol corresponding to a five-fold volume of the weight of the *Sophora japonica* fruit, and stirring the resulting solution at 75° C. for 5 hours. The resulting extract was filtered through a filter cloth to remove a precipitate, and thus to obtain a filtrate. The filtrate was concentrated under reduced pressure, and subjected to a spray drying process to prepare a *Sophora japonica* extract.

Meanwhile, broad-leaf bamboo (purchased from Samyoung Food Materials Ind., Co., Ltd.) was washed, and the broad-leaf bamboo leaves were separated. The washed broad-leaf bamboo leaves and purified water were at a weight ratio of 1:8, and the resulting mixture was extracted at 95° C.±2° C. for 4 hours. The extract was cooled to 75° C.±2° C., and filtered through a microfilter (5 μm). The filtrate was concentrated under reduced pressure to 35 to 40 Brix to prepare a broad-leaf bamboo extract.

Then, 0.02% by weight of xanthan gum was slowly added to 25 mL of purified water, and then hydrated at 40° C. for 10 minutes with stirring. 2% by weight of the *Sophora japonica* extract and 2% by weight of the broad-leaf bamboo extract were added while maintaining the xanthan gum-hydrated solution at 85° C., and then stirred to prepare a liquid food composition.

Example 2

A liquid food composition was prepared in the same manner as in Example 1, except that the xanthan gum was used at a content of 0.1% by weight.

Comparative Example 1

2% by weight of the *Sophora japonica* extract was added to 25 mL of purified water, and then stirred to prepare a liquid food composition.

Comparative Example 2

A liquid food composition was prepared in the same manner as in Example 1, except that the xanthan gum was used at a content of 0.2% by weight.

Experimental Example 1. Determination of Properties

The dispersibility, homogeneity and fluidity (flowability) of each of the liquid food compositions prepared in Examples and Comparative Examples were observed with the naked eye. These properties were evaluated according to the following criteria. The results obtained herein are listed in Table 1 and shown in FIGS. 1 and 2.

TABLE 1

|  | Dispersibility | Homogeneity | Fluidity |
|---|---|---|---|
| Example 1 | ○ | ○ | ○ |
| Example 2 | ○ | ○ | ○ |
| Comparative Example 1 | X | X | ○ |
| Comparative Example 2 | X | X | X |

Evaluation criteria
○: Good,
Δ: Mean,
X: Poor

Figure 2:
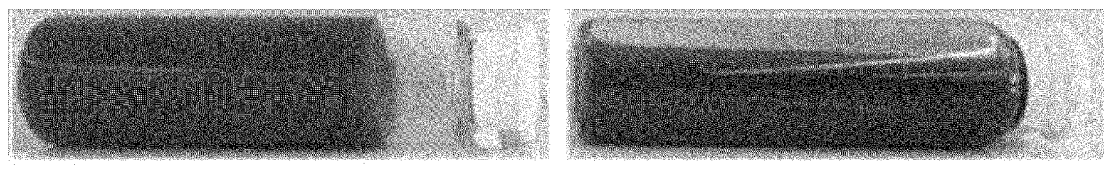
FIG. 2 is an image for evaluating the fluidity of the liquid food composition according to Experimental Example 1 of the present invention.

As listed in Table 1 and shown in FIGS. 1 and 2, it can be seen that the composition according to the present invention had superior dispersibility and fluidity, compared to the compositions of Comparative Examples. In particular, it can be seen that the compositions of Examples 1 and 2 had improved homogeneity because the components were uniformly dispersed in the solution, but not precipitated.

Formulation Example 1. Beverage

A beverage including the liquid food composition of the present invention was prepared according to a conventional method, based on the compositions and contents listed in Table 2 below.

TABLE 2

| Components | Content (Units: % by weight) |
|---|---|
| *Sophora japonica* extract | 2 |
| Red ginseng extract | 4 |

TABLE 2-continued

| Components | Content (Units: % by weight) |
|---|---|
| Broad-leaf bamboo | 2 |
| Xanthan gum | 0.05 |
| Pear concentrate | 3 |
| Liquid fructose | 4 |
| Purified water | Balance |

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A homogenous liquid composition comprising a *Sophora japonica* extract, a broad-leaf bamboo extract, and a xanthan gum, wherein the *Sophora japonica* extract is uniformly dispersed in the broad-leaf bamboo extract and xanthan gum.

2. The liquid composition of claim 1, wherein the *Sophora japonica* extract is a *Sophora japonica* fruit extract.

3. The liquid composition of claim 1, wherein the *Sophora japonica* extract is included in an amount of from 0.1 to 4% by weight, based on a total of 100% by weight of the liquid composition.

4. The liquid composition of claim 1, wherein the broad-leaf bamboo extract is included in an amount of from 0.1 to 5% by weight, based on a total of 100% by weight of the liquid composition.

5. The liquid composition of claim 1, wherein the xanthan gum is included in an amount of from 0.01 to 0.15% by weight, based on a total of 100% by weight of the liquid composition.

6. The liquid composition of claim 1, wherein the liquid composition has a viscosity at 25° C. ranging from 1 to 50 cPs.

7. A food comprising the liquid composition of claim 1.

* * * * *